(12) United States Patent
Bychkov

(10) Patent No.: US 10,734,112 B2
(45) Date of Patent: Aug. 4, 2020

(54) METHOD AND APPARATUS FOR TRANSMITTING DATA FROM SEVERAL RESPIRATORS

(71) Applicant: Loewenstein Medical Technology S.A., Luxembourg (LU)

(72) Inventor: Igor Bychkov, Ettlingen (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 115 days.

(21) Appl. No.: 15/927,162

(22) Filed: Mar. 21, 2018

(65) Prior Publication Data

US 2018/0277247 A1 Sep. 27, 2018

(30) Foreign Application Priority Data

Mar. 22, 2017 (DE) ........................ 10 2017 002 750

(51) Int. Cl.
*G16H 40/40* (2018.01)
*G16H 40/63* (2018.01)
*G16H 40/67* (2018.01)
*G16H 10/60* (2018.01)
*H04W 76/15* (2018.01)
*A62B 18/08* (2006.01)
(Continued)

(52) U.S. Cl.
CPC ............ *G16H 40/40* (2018.01); *A62B 18/08* (2013.01); *G16H 10/60* (2018.01); *G16H 40/63* (2018.01); *G16H 40/67* (2018.01); *H04B 7/155* (2013.01); *H04L 63/104* (2013.01); *H04W 76/15* (2018.02); *A62B 7/12* (2013.01); *A62B 18/02* (2013.01); *G08C 17/02* (2013.01); *H04L 9/3234* (2013.01)

(58) Field of Classification Search
None
See application file for complete search history.

(56) References Cited

U.S. PATENT DOCUMENTS 9,848,075 B1 * 12/2017 Ahmad ............ H04M 1/72527
2008/0097909 A1 4/2008 Dicks et al.
(Continued)

FOREIGN PATENT DOCUMENTS

DE 102015008946 A1 3/2016
EP 2392253 A1 12/2011
WO 2004070557 A2 8/2004

*Primary Examiner* — Anh Ngoc M Nguyen
(74) *Attorney, Agent, or Firm* — Abel Schillinger, LLP

(57) ABSTRACT

An apparatus and a method for the transmission of data from several respirators, each having at least one interface to a relay station and a data channel to the relay station. The data channel is unidirectional from the respirator to the relay station and supports at least two redundant technologies for the data transfer. The respirator data are encrypted and transmitted to the relay station, which decrypts the data, and authentication of the respirator and/or relay station takes place. Storage of the received data takes place in the relay station, as well as assignment of respirators and/or their data to particular users. The relay station comprises a forwarding interface for transmitting encrypted data to remote stations. A remote station is authenticated before the transmission, and data or user are selectively transmitted based on the authentication, the transmission being initiated by the relay station or the remote station.

20 Claims, 4 Drawing Sheets

(51) Int. Cl.
    *H04B 7/155* (2006.01)
    *H04L 29/06* (2006.01)
    *A62B 7/12* (2006.01)
    *A62B 18/02* (2006.01)
    *G08C 17/02* (2006.01)
    *H04L 9/32* (2006.01)

(56) References Cited

U.S. PATENT DOCUMENTS

| | | | |
|---|---|---|---|
| 2008/0271010 A1 | 10/2008 | Scholler et al. | |
| 2012/0182894 A1* | 7/2012 | Gaines | A61B 5/0022 370/252 |
| 2012/0226771 A1 | 9/2012 | Harrington et al. | |
| 2016/0058962 A1 | 3/2016 | Bychkov et al. | |

* cited by examiner

METHOD AND APPARATUS FOR TRANSMITTING DATA FROM SEVERAL RESPIRATORS

CROSS-REFERENCE TO RELATED APPLICATIONS

The present application claims priority under 35 U.S.C. § 119 of German Patent Application No. 102017002750.1, filed Mar. 22, 2017, the entire disclosure of which is expressly incorporated by reference herein.

BACKGROUND OF THE INVENTION

1. Field of the Invention

The present invention relates to a method and apparatus for transmitting data from several respirators.

2. Discussion of Background Information

Respirators are often fitted with an interface for data exchange with a network for the purposes of data exchange. Such an interface can be wired, for example implemented as an RJ45 data interface, or wireless, implemented for example as a WLAN, mobile telephone, IoT, M2M or Bluetooth interface.

A large amount of data can be exchanged over such a data interface. The software of the respirator can, for example, be updated by means of an update through access to remote data, as described in DE 10 2015 008 946 A1, the entire disclosure of which is incorporated by reference herein.

Treatment data, such as settings, measured values of therapeutic or physiological parameters, or also patient data, can furthermore be transmitted to a remote device, for example to a server, for storing and making it available for third parties, as described in EP 2 392 253 A1, the entire disclosure of which is incorporated by reference herein.

There is, however, in principle a possibility that an unauthorized data exchange occurs through the interface.

In view of the foregoing, it would be advantageous to have available a respirator that implements the data exchange more securely.

SUMMARY OF THE INVENTION

The present invention provides a method for the transmission of data from a large number of respirators (e.g., at least 5, 6, 7, 8, 9, 10, 15, 20, 25, 30, 40, 50, 60 or 100 respirators), each respirator comprising at least one interface to a relay station and each respirator comprising a data channel to the relay station. The data channel for data of the respirator that represent hours of use and/or the therapeutic quality is unidirectional from the device to the relay station, and supports at least two at least partially redundant technologies for the data transfer. The data of the respirator are encrypted and are transmitted in encrypted form to the relay station, and the relay station decrypts the data of the respirator, for example by means of a processor, and an authentication of the respirator and/or relay station takes place, for example making use of stored code or of the serial number of the respirator, the relay station recognizing the stored code or the serial number. A storage of the received data takes place in the relay station in a memory at least for a period of time that is sufficient for the data to be picked up at the forwarding interface, an assignment of the respirators and/or their data to particular users or user groups taking place in the relay station, so that the data are made available for forwarding specifically for the user or user groups that are assigned the devices and/or their data. The relay station comprises a forwarding interface for transmitting data to remote stations, for example web servers, PCs with ERP software, etc., the data being encrypted by the relay station and then transmitted via the forwarding interface to the remote station. The remote station decrypts the data and the remote station is authenticated before the transmission, and data or user or user group are selectively transmitted based on the authentication (wherein the remote station recognizes code or serial numbers based on stored data or keys). The transmission can be initiated by the relay station (push) or by the remote station (pull).

The invention also provides an apparatus for the transmission of data from a large number of respirators, each comprising at least one interface to a relay station and each comprising a data channel to the relay station. The data channel for data of the respirator that represent hours of use and/or the therapeutic quality is unidirectional from the device to the relay station, and supports at least two at least partially redundant technologies for the data transfer. The data of the respirator are encrypted and are transmitted in encrypted form to the relay station. The relay station decrypts the data of the respirator, for example by means of a processor, and an authentication of the respirator and/or relay station takes place, for example making use of stored code or of the serial number of the respirator, the relay station recognizing the stored code or the serial number. A storage of the received data takes place in the relay station in a memory at least for a period of time that is sufficient for the data to be picked up at the forwarding interface, an assignment of the respirators and/or their data to particular users or user groups taking place in the relay station, so that the data are made available for forwarding specifically for the user or user groups that are assigned the devices and/or their data. The relay station comprises a forwarding interface for transmitting data to remote stations, for example web servers, PCs with ERP software, etc., the data being encrypted by the relay station and then transmitted via the forwarding interface to the remote station. The remote station decrypts the data, and the remote station is authenticated before the transmission, and data or user or user group are selectively transmitted on the basis of the authentication (the remote station recognizing code or serial numbers based on stored data or keys). The transmission can be initiated by the relay station (push) or by the remote station (pull).

In one aspect of the invention, the code for authentication of the respirators, the relay station and/or the remote station may be formed as a certificate, preferably with a time-limited validity.

In another aspect or the invention, the two at least partially redundant technologies for the data transfer may include one or more of 2G, 3G, 4G, 5G mobile telephony with radio chips from different manufacturers, WIFI+Internet, Bluetooth+Internet, memory card+Internet, Lora, Sigfox or other radio standards for machine-to-machine communication In another aspect of the invention, the relay station may be a real or virtual computer, for example a web server, a file server, a server in the hospital or in the medical surgery, or a mobile terminal.

In another aspect of the invention, an encrypted temporary storage of the data may take place in the relay station.

In another aspect of the invention, the relay station may comprise a user access with configuration possibilities at least for the forwarding interface, for example the generation of tokens.

In another aspect of the invention, the assignment of devices to remote stations may be configured via the user access.

En another aspect of the invention, at least one of the editing, processing, evaluation, diagnosis, archiving or deletion of the data from the devices may be performed via the user access.

In another aspect of the invention, the remote configuration of the devices, for example the selection of one or more of the therapeutic pressures and modes, the adjustment of the humidifier settings and comfort settings, may be performed via the user access.

In another aspect of the invention, a remote servicing of the devices, evaluation of error messages, firmware updates from a distance, etc., may be made via the user access.

En another aspect of the invention, the user access may carry out an authentication of the users, for example by means of a 2-factor authentication.

In another aspect of the invention, the relay station may delete the data received from the devices from the memory after they have been picked up at the forwarding interface.

In another aspect of the invention, the relay station may delete the data received from the devices after a fixed period of time that can be set for the user or user group.

En another aspect of the invention, the relay station may delete the received data after a delete command that is received, for example, via the forwarding interface.

In another aspect of the invention, the relay station may comprise a data channel for patients, for example for speech, video or user inputs from the patient to a mobile terminal, for example a questionnaire on a smartphone.

In another aspect of the invention, the forwarding interface may exchange data over computer networks such as the Internet on the basis of HTTP or HTTPS, and/or may call up functions on remote computers.

In another aspect of the invention, the forwarding interface may comprise a uniform resource identifier URI, through which it can be uniquely identified, as well as an interface description in machine-readable format as an XML artefact, for example WSDL, which defines how to interact with the forwarding interface.

In another aspect of the invention, the communication with the forwarding interface may take place using protocols from the Internet context such as HTTP, and may be based on XML or JSON.

In another aspect of the invention, the forwarding interface may comprise a REST architecture.

In another aspect of the invention, the forwarding interface may perform an encryption with HTTPS.

In another aspect of the invention, the forwarding interface may connect the relay station and the remote station to one another directly, for example via a web API. An intermediate storage, for example in the form of files that are stored on an (S)FTP server, may not be necessary. This reduces the risk of the unauthorized access by third parties, and enables immediate success monitoring of the data forwarding.

In another aspect of the invention, the forwarding interface may authenticate the remote station by means of a user/user group identifier and with software tokens.

In another aspect of the invention, the remote station may query the data of a specific device identified, for example, by the serial number. If this is assigned in the assignment table of the relay station to the user or the user group for which the remote station is authenticated, the data are transmitted.

In another aspect of the invention, the remote station may request data without a specific serial number. The user or the user group for which the remote station is authenticated then receives the data of all the devices that are assigned to it in the assignment table of the relay station. This ensures that the data of all the devices that a user or a user group reports to the relay station are also forwarded. An assignment to the patient preferably takes place in the remote station.

In another aspect of the invention, for each user/user group in the relay station, a subset of device data may be specified which should be transmitted to the forwarding interface, for example only usage data, leakage, only AHI. This specification is preferably made by at least one administrator of the relay station or, alternatively, through different query commands from the remote station.

In another aspect of the invention, a counter may be incremented with every change to the content of the memory of the relay station, for example with every data record received from a therapeutic device. If a remote station queries data, then the current counter state is also transmitted to it via the forwarding interface. At the next query, the remote station can specifically query data that is new since the last counter status was transmitted to it. In this way the quantity of data transmitted is reduced to the data that has newly arrived. At the same time, the relay station remains without a state, and can be queried at its forwarding interface by a large number of remote stations, without having to store, for each individual remote station, which data record the said remote station received most recently.

In another aspect of the invention, at a request for new data from the remote station, the respective number of data records transmitted may be limited by an upper threshold, in order to avoid an overload of an interface, a network, a data store or data processing.

In another aspect of the invention, a remote station with a single token may query the data of a large number of users/user groups, provided the user at the relay station has entitled the remote station to fetch data for her. For this purpose, the remote station and the relay station transmit at least one identifier of at least one user while querying data. The relay station checks whether the remote station is authorized to query data of this user, and in the event that the authorization is present, transmits the data from devices of this user. Alternatively, the relay station may transmit the data of all devices of all users that have authorized the remote station to query their data, and adds an identifier of at least one user to whom the device is assigned as an attribute for each data record, so that the remote station only makes the data record concerned available to this user. The present invention also provides a respirator for use in an apparatus/method according to the invention, as well as a relay station for use in an apparatus/method according to the invention.

The invention primarily relates to respirators such as the APAP devices, bilevel devices, servo-ventilation devices, devices for home respiration and intensive respiration as well as emergency respirators. The invention relates to respirators that determine and store the usage duration and the therapeutic quality.

The therapeutic quality can, for example, be determined by considering the number of central, obstructive and mixed apneas within a specific period of time.

The therapeutic quality may also be determined by considering the number of central, obstructive and mixed hypopneas or RERAS or snoring periods or SpO2 desaturations within a specific period of time.

The therapeutic quality may also be determined by considering the duration and strength of Cheyne-Stokes breathing cycles within a specific period of time.

The therapeutic quality may also be determined by considering the duration and strength of a longer-term hypoventilation, measured through breathing (time) volume reduction and/or peak flow reduction and/or CO2 rise and/or oxygen saturation drop.

The therapeutic quality may also be determined by considering the occurrence and duration of unwanted situations, for example the occurrence of high leaks or disconnections, the occurrence of an absent synchronism between the respirator and the patient, or the occurrence of alarm situations or technical faults.

The therapeutic quality may initially be stored in an internal data memory of the device, and then forwarded to the relay station.

The usage duration of the respirator by the patient may, for example, be determined by considering the number of days and/or nights during which the therapy has been applied at least for a defined period of time.

The usage duration of the respirator may also be determined as the period of time for a single day during which a therapy has taken place.

The usage duration of the respirator may also be determined as the proportion of days and/or nights during which the therapy has been applied at least for a defined period of time.

The usage duration of the respirator may also be determined as an average therapeutic duration per calendar day and/or night, or as a period of time within which the respirator was switched on.

Specific conditions for which time segments when switched on are accepted for the therapeutic duration may be defined here, for example mask leaks below a specific threshold value, or the detection of breaths or the use of a breathing air humidifier.

The usage duration may initially be stored in an internal data memory of the device, and then forwarded to the relay station.

The servicing/function of the respirator may, for example, be determined by considering the observation of the intervals for the cleaning and/or exchange of at least one air filter, hose, or patient interface.

The servicing/function of the respirator may, for example, be determined by considering known, saved fault states of the respirator.

The servicing/function of the respirator may, for example, be determined by considering version statuses of at least one device software or of at least one item of device electronics.

The servicing/function of the respirator may, for example, be determined by considering a serial number, a manufacturer ID, a UID, a network subscriber number and an identification of the device type.

The servicing/function of the respirator may, for example, be determined by considering the current therapeutic mode and the current therapeutic settings, for example pressure and frequency settings, the current device settings, for example language, date, time, or the current comfort settings, for example humidifier level, initial pressure drop, or autostart.

The servicing/function may initially be stored in an internal data memory of the device, and then forwarded to the relay station.

BRIEF DESCRIPTION OF THE DRAWINGS

Further benefits and features of the present invention will emerge from the description of the exemplary embodiments, which will be explained with reference to the accompanying drawings.

In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
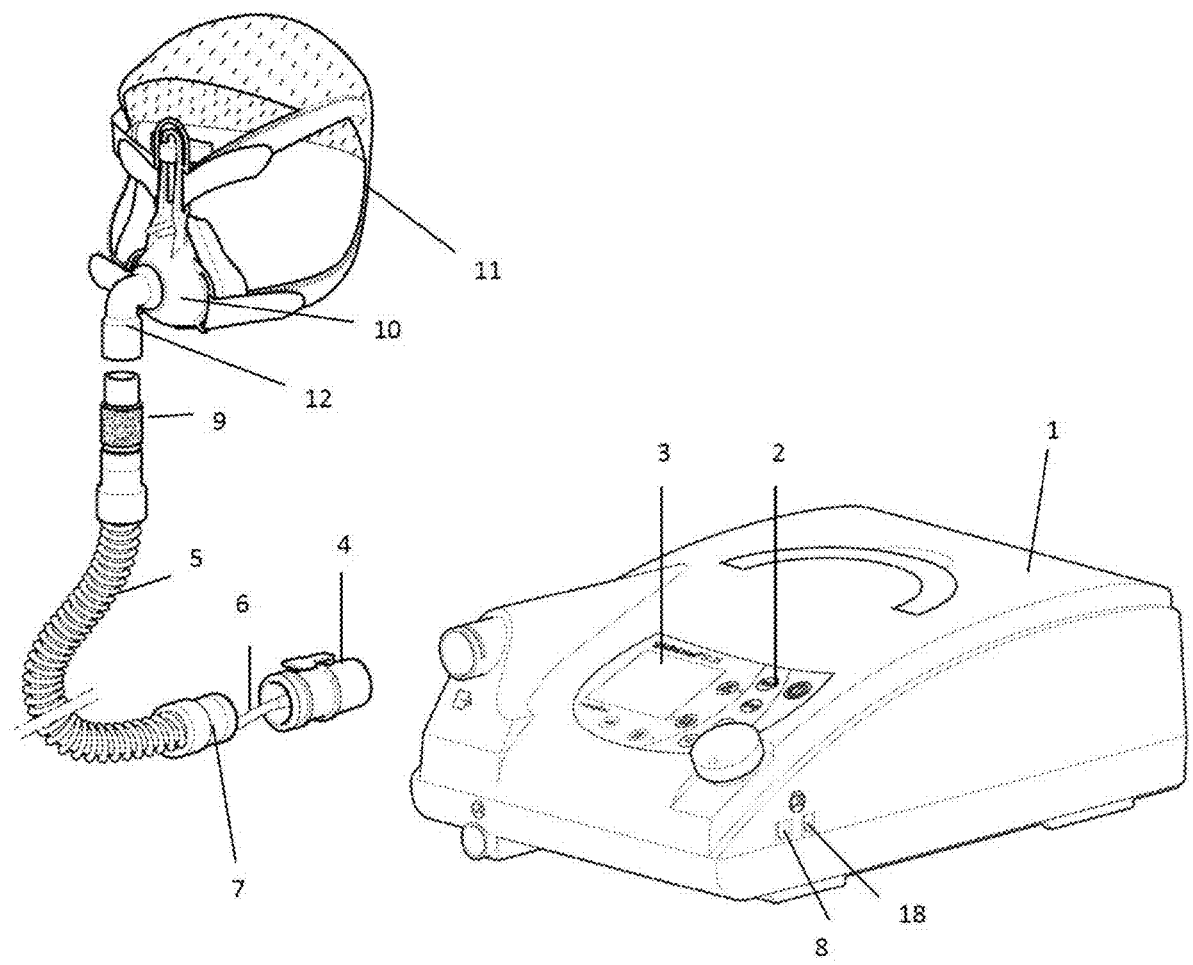
FIG. 1 shows the fundamental structure of a respirator with a patient interface.

FIG. 1 shows the fundamental structure of a respirator (1). A breathing gas pump is arranged in an interior space in the device in the region of a device housing with an operating panel (2) as well as a display (3). A connecting hose (5) is connected via a coupling (4). An additional pressure measuring hose (6) can run along the connecting hose (5), and is connectable via a pressure inlet nozzle (7) to the device housing. The device housing (1) comprises at least one interface (8, 18) to permit data transmission. A humidifier can be fitted by means of an adapter.

An exhalation element (9) is arranged in the region of an extension to the connecting hose (5) facing away from the device housing (1). An exhalation valve can also be used.

FIG. 1 also shows a patient interface, formed as a breathing mask (10), implemented here by way of example as a nasal mask, Fixing in the region of a head of a patient can be achieved by means of a headgear (11). In the region of its extension facing towards the connecting hose (5) the patient interface (10) comprises a coupling element (12).

The input and/or output of data, such as for example dead space volume, can be achieved through the interface (8, 18). The interfaces can be implemented in wired form, as an infrared interface, as a Bluetooth interface, as a mobile phone interface, IoT or M2M interface or as a USB.

The respirator (1) according to the invention may be designed such that it can be connected to a patient via a hose and a patient interface in order to provide respiration. It comprises a source for breathing gas which is, for example, designed as an electric motor with a fan wheel, and a device for determining pressure and/or flow and/or volume of the breathing gas, as well as a control unit which is designed such that for each breathing cycle it determines a breathing gas pressure on the basis of a predetermined value for the patient and/or on the basis of measurement signals for the parameters of pressure and/or flow and/or volume, and regulates the source for breathing gas such that the breathing gas pressure is generated.

The respirator has a memory (31) for storing data that represent the usage period and the therapeutic quality and, in addition, the function/servicing of the device.

The control unit may, furthermore, be designed such that it determines the current pressure and/or flow and/or the volume of breathing gas, and represents the current value via a display connected to the control unit. The control unit may, moreover, be designed such that it determines trend changes in its calculations over time based on one or more parameters, wherein the trend changes may be displayed on the display.

Displayed data can also be transmitted via a modem or another interface (18).

Figure 2:
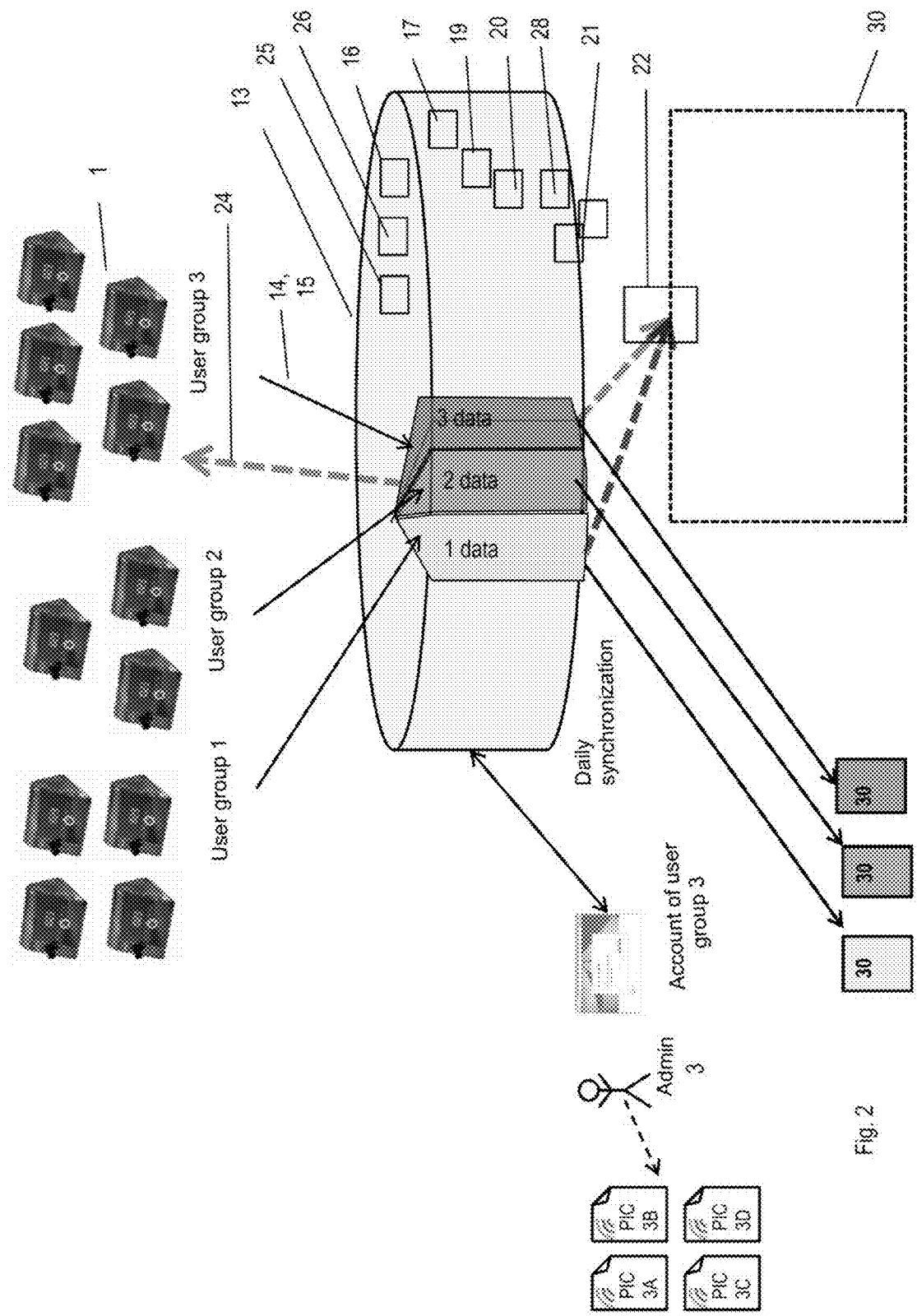
FIG. 2 shows an apparatus with several respirators, each comprising an interface to a relay station and a data channel to the relay station.

FIG. 2 shows an apparatus with a large number of respirators (1), each with at least one interface (8, 18) to a relay station (13), and each with a data channel (14) to the relay station, wherein the data channel (14) is unidirectional from the device (1) to the relay station (13) at least for data of the respirator that represent usage hours or the therapeutic quality. The data channel (14) supports at least two at least partially redundant technologies (15) for the data transfer, wherein an encryption (16) of the data channel is performed, and wherein an authentication (17) of the respirator (1) and the relay station (13) is performed. A storage of the received data in a memory (19) takes place in the relay station (13) for at least a period of time that is sufficient for the data to be picked up at the forwarding interface (28). In addition, the relay station performs an assignment (20) of the respirators and/or their data to specific users or user groups, so that the data are made available for forwarding specifically for the user or user group to which the devices and/or their data are assigned.

The relay station (13) comprises a forwarding interface (28) for transferring data to remote stations (30) (for example, web servers, PCs with ERP software, etc.), wherein the data are encrypted (21) by the relay station (13) and then transmitted via the forwarding interface (28) to the remote station (30). Before the transmission, the remote station (30) is authenticated (22) and data (user or user group) are selectively transmitted on the basis of the authentication, wherein the transmission can be initiated by the relay station (push) or by the remote station (pull, query).

The apparatus is a wired or wireless telecommunication network such as, for example, a computer network, a virtual private network (VPN), an intranet, extranet or the Internet.

The relay station (13) comprises at least one real or virtual processor (26) for executing a program (40), as well as a component for storing and/or generating a data key.

To store the data (32) from the respirator (1), the procedure is, for example, as follows:

With the aid of the data key (34), the data (32) are encrypted, and transmitted by the respirator via the interface (18) and the data line (14) to the relay station (13). The relay station (13) stores the encrypted data in a free area of memory.

Preferably, the encrypted data is stored together with an index identifier of the respirator and/or user data. The index identifier of the respirator can be a serial number. The user data can be a patient ID or a care person ID.

The remote station (30) can query the data of a specific device (identified, for example, by the serial number). If this is assigned in the assignment table (20) of the relay station (13) to the user or the user group for which the remote station (30) is authenticated, the data are transmitted.

Alternatively, the remote station (30) may request data without a specific serial number, whereupon the user or the user group for which the remote station (30) is authenticated receives the data of all the devices that are assigned to it in the assignment table (20) of the relay station (13). This ensures that the data of all the devices (1) that a user or a user group reports to the relay station (13) are also forwarded. An assignment to the patient preferably takes place in the remote station (30).

A subset of device data can be specified in the relay station (13) for every user/user group, which subset is to be transmitted to the forwarding interface (28), for example only leakage, only AHI, etc. This specification is preferably made by at least one administrator of the relay station (13) or, alternatively, through different query commands from the remote station (30).

SyncID: A counter is incremented with every change to the content of the memory (19) of the relay station (13), for example with every data record received from a therapeutic device. If a remote station (30) queries data, then the current counter state is also transmitted to it via the forwarding interface (28). At the next query, the remote station (30) can specifically query data that is new since the last counter status was transmitted to it. In this way the quantity of data transmitted is reduced to the data that has newly arrived. At the same time, the relay station (13) remains without a state, and can be queried at its forwarding interface (28) by a large number of remote stations (30), without having to store, for each individual remote station (30), which data record the said remote station received most recently.

A remote station (30) (with a single token) can query the data of a large number of users/user groups, provided the user at the relay station (13) has entitled the remote station (30) to fetch data for him. For this purpose the remote station (30) and the relay station (13) transmit at least one identifier of at least one user during the querying of data. The relay station (13) checks whether the remote station (30) is authorized to query data of this user, and in the event that the authorization is present, transmits the data from devices of this user. Alternatively, the relay station transmits the data of all devices of all users that have authorized the remote station (30) to query their data, and adds an identifier of at least one user to whom the device is assigned as an attribute for each data record, so that the remote station (30) only makes the data record concerned available to this user.

Figure 3:
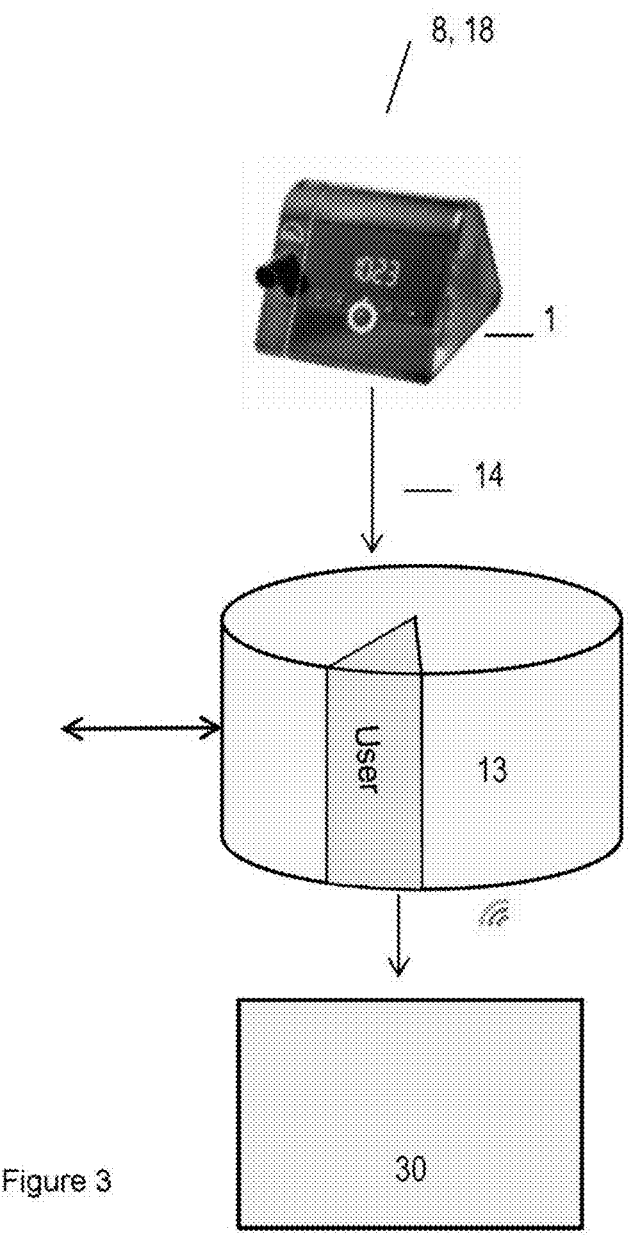
FIG. 3 shows an apparatus with a respirator, with at least one interface to a relay station and a data channel to the relay station.

FIG. 3 shows an apparatus with a respirator (1), with at least one interface (8, 18) to a relay station (13), and with a data channel (14) to the relay station, wherein the data channel (14) is unidirectional from the device (1) to the relay station (13) at least for data of the respirator that represent the usage hours or the therapeutic quality. The data channel (14) supports at least two at least partially redundant technologies (15) for the data transfer, wherein an encryption (16) of the data channel is performed, and wherein an authentication (17) of the respirator (1) and the relay station (13) is performed. A storage of the received data in a memory (19) takes place in the relay station (13) for at least a period of time that is sufficient for the data to be picked up at the forwarding interface (28). In addition, the relay station performs assignment (20) of the respirators and/or their data to specific users or user groups, so that the data are made available for forwarding specifically for the user or user group to which the devices and/or their data are assigned.

The relay station (13) comprises a forwarding interface (28) for transferring data to remote stations (30) (for example, web servers, PCs with ERP software, etc.), wherein the data are encrypted (21) by the relay station (13)

and then transmitted via the forwarding interface (28) to the remote station (30). Before the transmission, the remote station (30) is authenticated (22) and data (user or user group) are selectively transmitted on the basis of the authentication, wherein the transmission can be initiated by the relay station (push) or by the remote station (pull, query).

The respirator is for example authenticated by inserting an SD card and assigned to a user group. The authentication proceeds, for example, via a modem which is connected to the respirator, at the relay station (13). The relay station (13) forwards the data of the respirator or of the authentication to the remote station (30).

Figure 4:
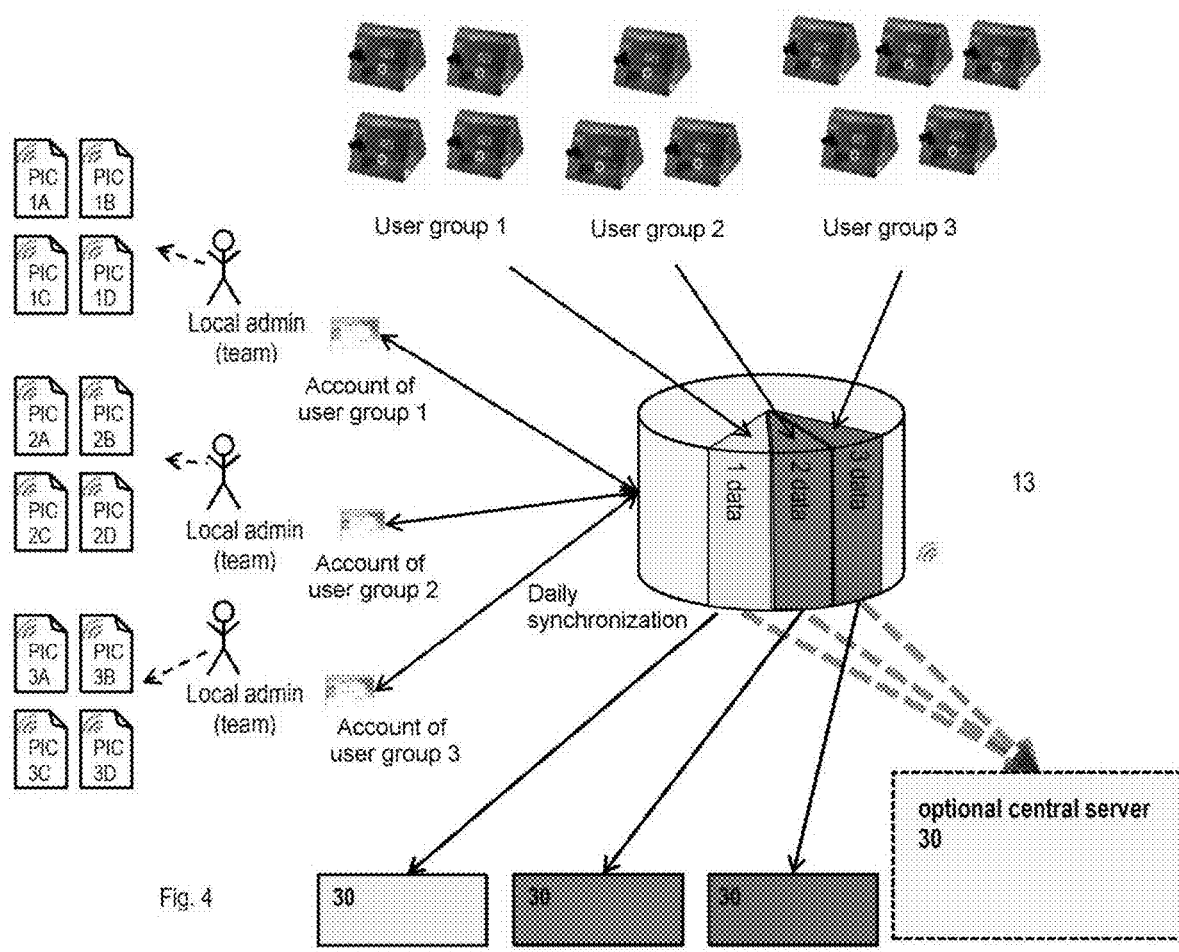
FIG. 4 shows an apparatus with several respirators that are grouped into different user groups.

FIG. 4 shows an apparatus with several respirators (1) that are grouped into different user groups. The respirators transmit data to one (or more) relay stations (13). The relay station (13) comprises user-specific (memory) regions. A storage of the received data in a memory (19) takes place in the relay station (13) for at least a period of time that is sufficient for the data to be picked up at the forwarding interface (28), In addition, the relay station performs assignment (20) of the respirators and/or their data to specific users or user groups, so that the data are made available for forwarding specifically for the user or user group to which the devices and/or their data are assigned.

The relay station (13) comprises a forwarding interface (28) for transferring data to remote stations (30) (for example, web servers, PCs with ERP software, etc.), wherein the data are encrypted (21) by the relay station (13) and then transmitted via the forwarding interface (28) to the remote station (30). Before the transmission, the remote station (30) is authenticated (22) and data (user or user group) are selectively transmitted on the basis of the authentication, wherein the transmission can be initiated by the relay station (push) or by the remote station (pull, query). The remote stations can be physically separate remote stations. A remote station (30) that only manages the data specifically for the user or user group can also be provided.

The respirator is for example authenticated by inserting an SD card and assigned to a user group. The authentication proceeds, for example, via a modem which is connected to the respirator, at the relay station (13). The relay station (13) forwards the data of the respirator or of the authentication to the remote station (30).

Administrators of the respective user group can access the relay station through a specific user-group account in order, for example, to effect settings at the relay station or to query data.

What is claimed is:

1. A method for the transmission of data from two or more respirators, wherein each respirator comprises at least one interface to a relay station and a data channel, unidirectional from the respirator to the relay station and supporting at least two at least partially redundant technologies for data transfer, for data of the respirator that represent hours of use and/or therapeutic quality, the relay station comprising a memory for data received from a respirator and a forwarding interface for transmitting received data to a remote station, and wherein the method comprises:

encryption of data of a respirator and transmission of the encrypted data to the relay station, authentication of respirator and/or relay station by a stored code or a serial number recognized by the relay station, decryption of the encrypted data of the respirator by the relay station and storing the decrypted data in the memory of the relay station, picking up the stored data at the forwarding interface, assignment of a respirator and/or its data to a particular user or a particular user group by the relay station, so that the data are made available for forwarding specifically for the user or user group that is assigned the devices and/or their data, transmission of the stored data to the remote station by the forwarding interface after encryption of the data by the relay station, the transmission being initiated by the relay station or by the remote station, decryption of the transmitted data by the remote station, authentication of the remote station before the transmission of data and transmitting data or user or user group selectively on the basis of the authentication, the remote station recognizing code or serial numbers on the basis of stored data or keys.

2. A system for the transmission of data from two or more respirators, wherein the system comprises, in addition to the two or more respirators, a relay station comprising a memory and a forwarding interface, as well as a remote station, and wherein each respirator comprises at least one interface to the relay station and a data channel to the relay station, which data channel represents hours of use and/or therapeutic quality, is unidirectional from the respirator to the relay station, and supports at least two at least partially redundant technologies for data transfer, wherein the data of the respirator are encrypted and transmitted in encrypted form to the relay station, wherein the relay station is configured to decrypt the data of the respirator, wherein the respirator and/or the relay station are configured to be capable of being authenticated, wherein the memory of the relay station is configured to store the received data and the forwarding interface of the relay station is configured to pick up the stored data from the memory and transmit the picked-up stored data to the remote station, wherein the relay station is configured to assign a respirator and/or its data to a particular user or user group, so that the data are made available for forwarding specifically for the user or user group that is assigned the devices and/or their data, and is configured to encrypt data prior to transmission thereof to the remote station by the forwarding interface, wherein the remote station is configured to decrypt the data and to be capable of being authenticated before the transmission, wherein data for user/user group can selectively be transmitted on the basis of the authentication, and wherein the transmission can be initiated by the relay station or by the remote station.

3. The system of claim 2, wherein the two at least partially redundant technologies for the data transfer comprise one or more of 2G, 3G, 4G, 5G mobile telephony with radio chips from different manufacturers, WIFI+Internet, Bluetooth+Internet, memory card+Internet, Lora, Sigfox.

4. The system of claim 2, wherein the relay station is a real or virtual computer.

5. The system of claim 2, wherein an encrypted intermediate storage of the data takes place in the relay station.

6. The system of claim 2, wherein the relay station comprises a user access with configuration possibilities at least for the forwarding interface.

7. The system of claim 2, wherein an assignment of a respirator to a remote station is configured via a user access and/or at least one of editing, processing, evaluation, diagnosis, archiving or deletion of data from a respirator is performed via a user access.

8. The system of claim 2, wherein a remote configuration of a respirator is performed via a user access and/or a remote servicing of a respirator is performed via a user access.

9. The system of claim 2, wherein a user access carries out an authentication of a user.

10. The system of claim 2, wherein the relay station deletes data received from a respirator from a memory (i) after the data have been picked up at the forwarding interface or (ii) after a fixed period of time that can be set for a user or user group or (iii) after a delete command.

11. The system of claim 2, wherein the relay station further comprises a data channel for a patient.

12. The system of claim 2, wherein the forwarding interface is configured to exchange data over computer networks and calling up functions on remote computers.

13. The system of claim 2, the forwarding interface comprises a uniform resource identifier (URI) through which it can be uniquely identified, as well as an interface description in machine-readable format, which defines how to interact with the forwarding interface.

14. The system of claim 2, wherein communication with the forwarding interface takes place using protocols from an Internet context and is based on XML or JSON.

15. The system of claim 2, wherein the forwarding interface has a REST architecture and/or is configured to carry out an encryption with HTTPS and/or to authenticate the remote station by a user/user group identifier and with software tokens.

16. The system of claim 2, wherein the remote station is configured to query data of a specific respirator, and data are transmitted if the respirator is assigned in an assignment table of the relay station to a user or a user group for which the remote station is authenticated.

17. The system of claim 2, wherein the remote station is configured to request data without a specific serial number and a user or a user group for which the remote station is authenticated receives data of all respirators that are assigned to it in an assignment table of the relay station.

18. The system of claim 2, wherein a subset of respirator data which is transmitted to the forwarding interface is specified for each user/user group in the relay station.

19. The system of claim 2, wherein a counter is incremented with each change to a content of the memory of the relay station, and a current counter state is also transmitted via the forwarding interface in response to a data query.

20. The system of claim 2, wherein the remote station is configured to query data of many users/user groups, provided a user/user group has entitled the remote station at the relay station to pick up data for it, for which purpose the remote station and the relay station transmit at least one identifier of at least one user during a data query.

* * * * *